United States Patent
Southwell et al.

(10) Patent No.: US 10,279,175 B2
(45) Date of Patent: *May 7, 2019

(54) SYSTEM, DEVICE AND GARMENT FOR DELIVERING TRANSCUTANEOUS ELECTRICAL STIMULATION

(71) Applicant: GI Therapies Pty Ltd, Melbourne, Victoria (AU)

(72) Inventors: Bridget Rae Southwell, Victoria (AU); David Fisher, New South Wales (AU); Rod Wiebenga, Victoria (AU); Lisa Tjernberg, Victoria (AU)

(73) Assignee: GI Therapies Pty Ltd, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,654

(22) Filed: Mar. 29, 2018

(65) Prior Publication Data

US 2018/0289955 A1    Oct. 11, 2018

Related U.S. Application Data

(63) Continuation of application No. 15/028,191, filed as application No. PCT/AU2014/000968 on Oct. 10, 2014, now Pat. No. 9,962,544.

(30) Foreign Application Priority Data

Oct. 11, 2013  (AU) ................ 2013903922
Oct. 11, 2013  (AU) ................ 2013903926

(51) Int. Cl.
*A61N 1/32* (2006.01)
*A61N 1/22* (2006.01)
(Continued)

(52) U.S. Cl.
CPC ............ *A61N 1/321* (2013.01); *A61N 1/048* (2013.01); *A61N 1/0452* (2013.01);
(Continued)

(58) Field of Classification Search
CPC .. A61N 1/0484; A61N 1/36014; A61N 1/321; A61N 1/22
See application file for complete search history.

(56) References Cited

U.S. PATENT DOCUMENTS

| 4,381,012 A | 4/1983 | Russek |
| 4,690,144 A | 9/1987 | Rise et al. |

(Continued)

FOREIGN PATENT DOCUMENTS

| GB | 960682 | 6/1964 |
| JP | 02-206475 | 8/1990 |

(Continued)

OTHER PUBLICATIONS

Chase et al., 2005, Pilot Study Using Transcutaneous Electrical Stimulation (Interferential Current) to Treat Chronic Treatment-Resistant Constipation and Soiling in Children, Journal of Gastroenterology and Hepatology, 20:1054-1061.

(Continued)

*Primary Examiner* — Alyssa M Alter
(74) *Attorney, Agent, or Firm* — Knobbe Martens Olson & Bear LLP

(57) ABSTRACT

An electrode connector assembly for the use in transcutaneous electrical stimulation includes a flexible web extending in a plane and first, second, third and fourth electrode connectors carried by the web and spaced from each other about the web in the plane. The electrode connector assembly further includes an electrical connector and first, second, (Continued)

third and fourth conductors electrically coupling the respective first, second, third and fourth electrode connectors to the electrical connector.

20 Claims, 10 Drawing Sheets

(51) Int. Cl.
*A61N 1/04* (2006.01)
*A61N 1/36* (2006.01)

(52) U.S. Cl.
CPC ......... *A61N 1/0456* (2013.01); *A61N 1/0484* (2013.01); *A61N 1/22* (2013.01); *A61N 1/323* (2013.01); *A61N 1/36007* (2013.01); *A61N 1/36014* (2013.01)

(56) References Cited

U.S. PATENT DOCUMENTS

| | | | |
|---|---|---|---|
| 5,562,717 | A | 10/1996 | Tippey et al. |
| 5,871,534 | A | 2/1999 | Messick et al. |
| 6,445,955 | B1 | 9/2002 | Michelson et al. |
| 6,728,577 | B2 | 4/2004 | Minogue et al. |
| 8,000,792 | B1 | 8/2011 | Dechev et al. |
| 8,019,426 | B2 | 9/2011 | Moore et al. |
| 9,789,308 | B2 | 10/2017 | Southwell et al. |
| 9,827,418 | B2 | 11/2017 | Southwell et al. |
| 9,861,816 | B2 | 1/2018 | Southwell et al. |
| 9,962,544 | B2 * | 5/2018 | Southwell ............... A61N 1/22 |
| 2004/0030267 | A1 | 2/2004 | Orten |
| 2005/0055054 | A1 | 3/2005 | Yu |
| 2005/0075678 | A1 | 4/2005 | Faul |
| 2005/0278001 | A1 | 12/2005 | Qin et al. |
| 2006/0009815 | A1 | 1/2006 | Boveja |
| 2006/0089683 | A1 | 4/2006 | Hagglof et al. |
| 2006/0184211 | A1 | 8/2006 | Gaunt et al. |
| 2006/0195153 | A1 | 8/2006 | Diubaldi et al. |
| 2007/0055337 | A1 | 3/2007 | Tanrisever |
| 2007/0150034 | A1 | 6/2007 | Rooney |
| 2007/0156183 | A1 | 7/2007 | Rhodes |
| 2007/0255085 | A1 | 11/2007 | Kishawi et al. |
| 2008/0077192 | A1 | 3/2008 | Harry |
| 2008/0147143 | A1 | 6/2008 | Dejan Popovic et al. |
| 2008/0208287 | A1 | 8/2008 | Palermo |
| 2008/0249591 | A1 | 10/2008 | Gaw et al. |
| 2009/0048642 | A1 | 2/2009 | Goroszeniuk |
| 2009/0157149 | A1 | 6/2009 | Wahlgren et al. |
| 2009/0182393 | A1 | 7/2009 | Bachinski |
| 2010/0049027 | A1 | 2/2010 | Teschner et al. |
| 2010/0152817 | A1 | 6/2010 | Gillbe |
| 2011/0015689 | A1 | 1/2011 | Rhodes |
| 2011/0230701 | A1 | 9/2011 | Simon |
| 2011/0295339 | A1 | 12/2011 | Carroll |
| 2012/0029591 | A1 | 2/2012 | Simon |
| 2012/0116477 | A1 | 5/2012 | Crowe et al. |
| 2013/0123568 | A1 | 5/2013 | Hamilton et al. |
| 2017/0182318 | A1 | 6/2017 | Fisher et al. |
| 2017/0348526 | A1 | 12/2017 | Southwell et al. |
| 2018/0133468 | A1 | 5/2018 | Southwell et al. |
| 2018/0154145 | A1 | 6/2018 | Southwell et al. |

FOREIGN PATENT DOCUMENTS

| | | |
|---|---|---|
| JP | 08-501946 | 3/1996 |
| JP | 10-179768 | 7/1998 |
| JP | 2001-170190 | 6/2001 |
| JP | 2001-238967 | 9/2001 |
| JP | 2007-037853 | 2/2007 |
| JP | 2008-307382 | 12/2008 |
| JP | 2009-136585 | 6/2009 |
| WO | WO 08/137162 | 11/2008 |
| WO | WO 11/026166 | 3/2011 |
| WO | WO 12/116407 | 9/2012 |
| WO | WO 15/051405 | 4/2015 |
| WO | WO 15/051406 | 4/2015 |

OTHER PUBLICATIONS

Chase et al., Abstract for oral presentation on "Daily transcutaneous electrical stimulation (using interferential current) at home increased defecation in children with slow transit constipation: a pilot study," Neurogastroenterology and Motility 2009, Joint International Meeting, Chicago Aug. 27-30, Abstract published on Jul. 1, 2009, p. 3.
Clarke et al., 2009, Decreased colonic transit time after transcutaneous interferential electrical stimulation in children with slow transit constipation, Journal of Pediatric Surgery, 44(2):408-412.
Clarke et al., 2009, Improvement of quality of life in children with slow transit constipation after treatment with transcutaneous electrical stimulation. J Pediatr Surg, 44: 1268-1273.
Clarke et al., 2012, Transabdominal electrical stimulation increases colonic propagating pressure waves in paediatric slow transit constipation. J Pediatr Surg. 47(12):2279-2284.
De Paepe et al., 2002, The role of pelvic-floor therapy in the treatment of lower urinary tract dysfunctions in children, Scand J Urol Nephrol. 36(4):260-267 (abstract).
Ismail et al., Dec. 2009, Daily transabdominal electrical stimulation at home increased defecation in children with slow-transit, J Pediatr Surg, 44: 2388-2392.
Ismail et al., Daily transcutaneous electrical stimulation at home increased defecation in children with slow transit constipation: a pilot study, 42nd Annual Meeting of Pacific Association of Pediatric Surgeons, May 10-14, 2009, Hong Kong, abstract, pp. 216-217.
Ismail et al., J Pediatr Surg website screen capture showing article preview with publication date of Dec. 2009 for article Daily transabdominal electrical stimulation at home increased defecation in children with slow-transit, J Pediatr Surg, 44: 2388-2392 (retrieved on Jul. 28, 2017, from: http://www.jpedsurg.org/article/S0022-3468(09)00640-X/pdf).
Ismail et al., PubMed website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).
Ismail et al., ScienceDirect website screen capture showing article preview with publication date of Dec. 2009 for article "Daily transabdominal electrical stimulation at home increased defecation in children with slow-transit," J Pediatr Surg, 44: 2388-2392 (retrieved on Jul. 28, 2017, from: http://www.sciencedirect.com/science/article/pii/S002234680900640X).
Kajbafzadeh et al., 2012, Transcutaneous interferential electrical stimulation for management of neurogenic bowel dysfunction in children with myelomeningocele. Int J Colorectal Dis, 27:453-458.
Koklu et al., May 2010, Clinical trial: interferential electric stimulation in functional dyspepsia patents—a prospective randomized study, Aliment Pharmacol Ther, 31:961-968.
Leong et al., 2001, Long-term effects of transabdominal electrical stimulation in treating children with slow-transit constipation, Journal of Pediatric Surgery, 46:2309-2312.
Queralto et al., Interferential Therapy: a new treatment for slow transit constipation. A pilot study in adults. Colorectal Dis, 2012: 15: e35-e39.
Sikiru et al., Nov.-Dec. 2008, Transcutaneous electrical nerve stimulation (TENS) in the symptomatic management of chronic prostatitis/chronic pelvic pain syndrome: a placebo-control randomized trial, International Braz J Urol., 34(6):708-713.
Southwell, 2013, Medical devices to deliver transcutaneous electrical stimulation using interferential current to treat constipation, Expert Rev. Med. Devices, 19(6):701-704.
Southwell, B. Treatment of slow transit constipation in children. Fifth European Paediatric Motility Meeting, J Pediatr Gastroenterol Nutr 2011; 53: Suppl 2 s 551-3.

(56) References Cited

OTHER PUBLICATIONS

Stillman et al., 2006, Strengthening of the pelvic floor muscles using transcutaneous magnetic nerve stimulation: a review of the literature. Australian and New Zeland Continence Journal. 12(2):31-40.
Veiga ML, Lordêlo P, Farias T, Barroso U Jr. Evaluation of constipation after parasacral transcutaneous electrical nerve stimulation in children with lower urinary tract dysfunction—a pilot study. J Pediatr Urol. 2013; 9(5):622-6.
Vitton et al., 2009, Transcutaneous Posterior Tibial Nerve Stimulation for Fecal Incontinence in Inflammatory Bowel Disease Patients: A Therapeutic Option?, Inflammatory Bowel Diseases, 15(3):402-405.
Yik et al., 2011, Slow-transit constipation with concurrent upper gastrointestinal dysmotility and its response to transcutaneous electrical stimulation. J Pediatr Surg Int, 27(7):705-711.
Yik et al., 2012, Home transcutaneous electrical stimulation to treat children with slow-transit constipation, Journal of Pediatric Surgery, 47:1285-1290.
Yik et al., 2012, The impact of transcutaneous electrical stimulation therapy on appendicostomy operation rates for children with chronic constipation—a single-institution experience, Journal of Pediatr Surg, 47: 1421-1426.
Yik et al., 2013, Home Transcutaneous Electrical Stimulation (TES) Therapy to Treat Children with Anorectal Retention (AR): A Pilot Study. Gastroenterology, 144(5):5364.
Yik et al., 2013, Treatment Resistant Slow-Transit Constipation (STC) in Children Can Be Improved With Home-Based Transcutaneous Electrical Stimulation. Gastroenterology, 144(5):S399.

\* cited by examiner

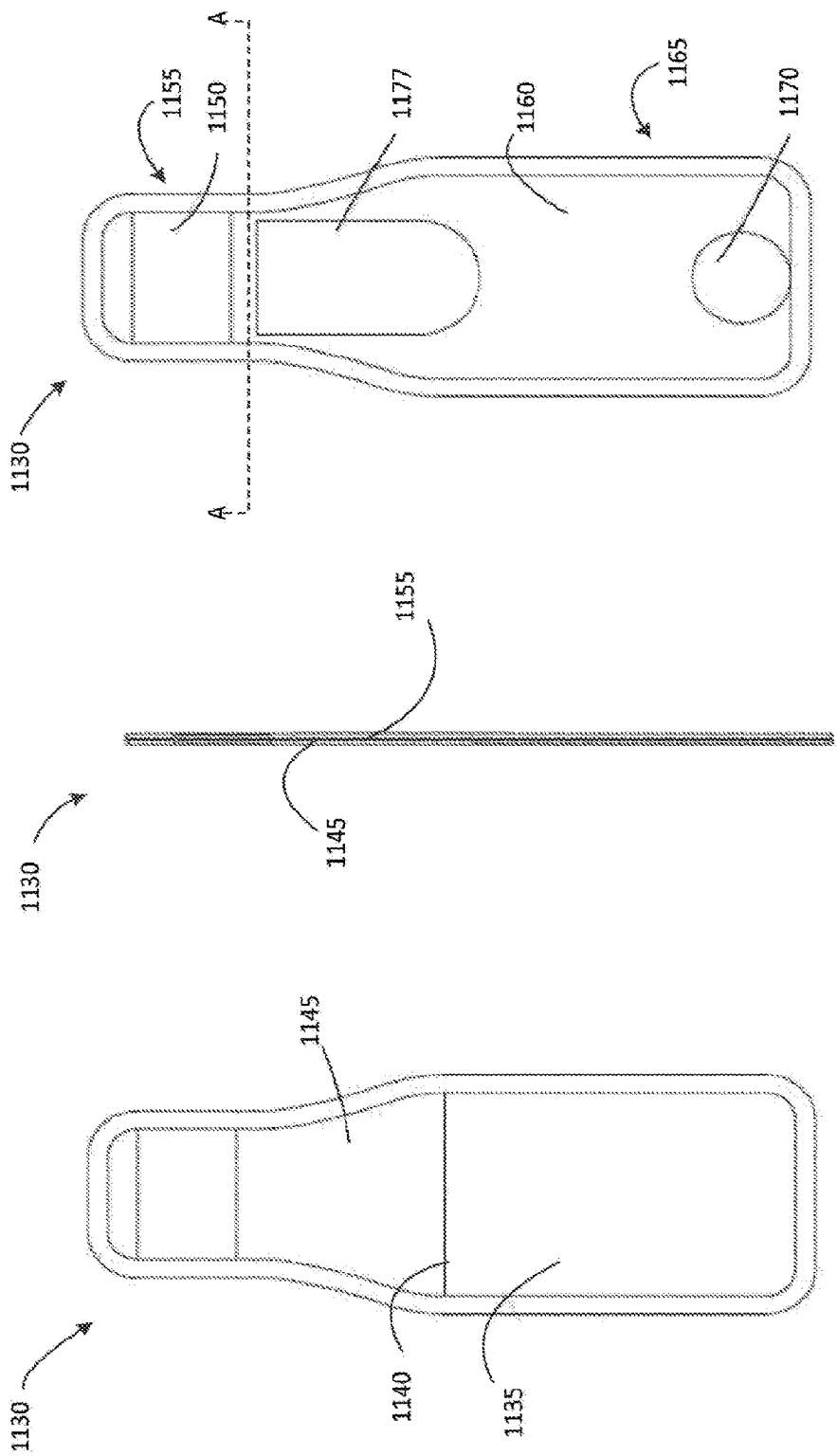

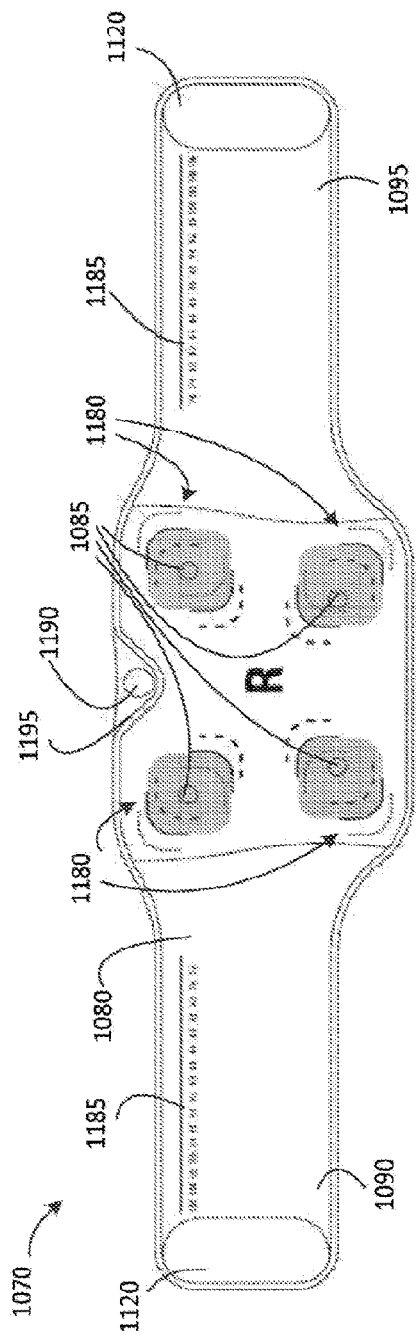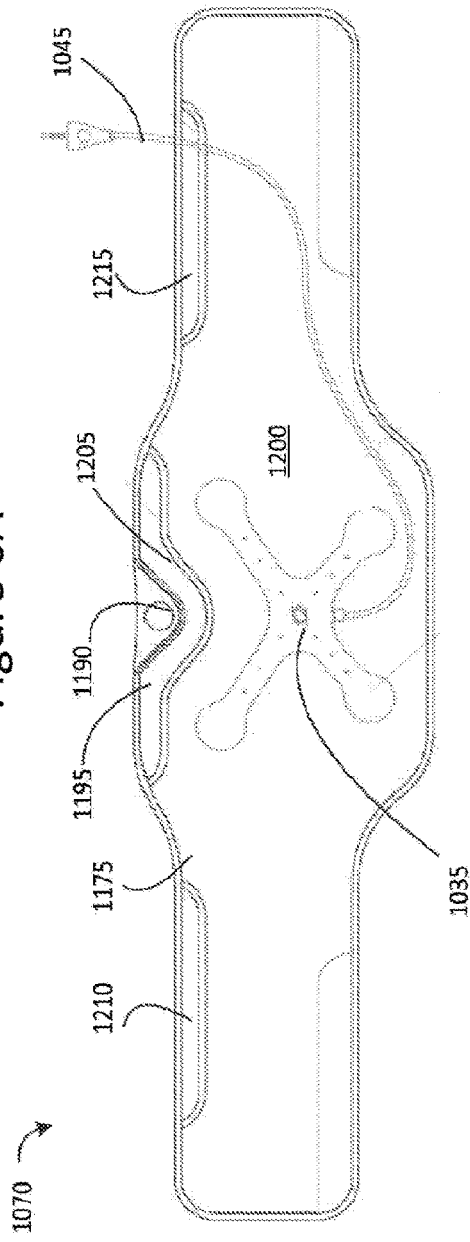

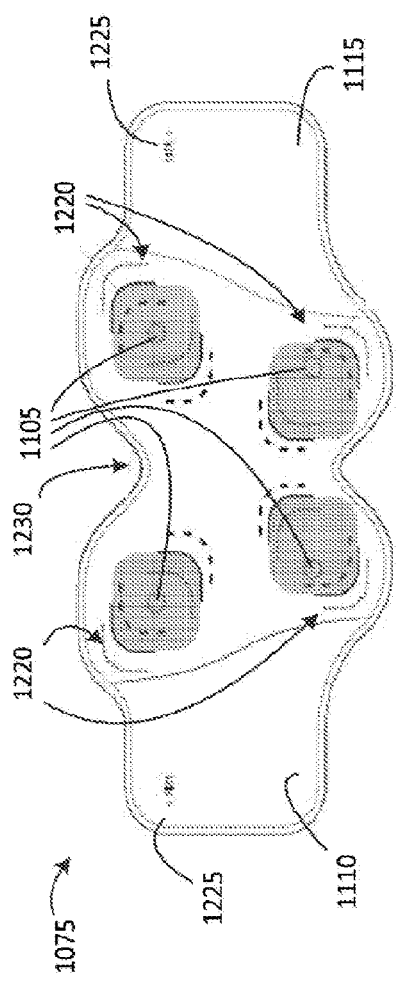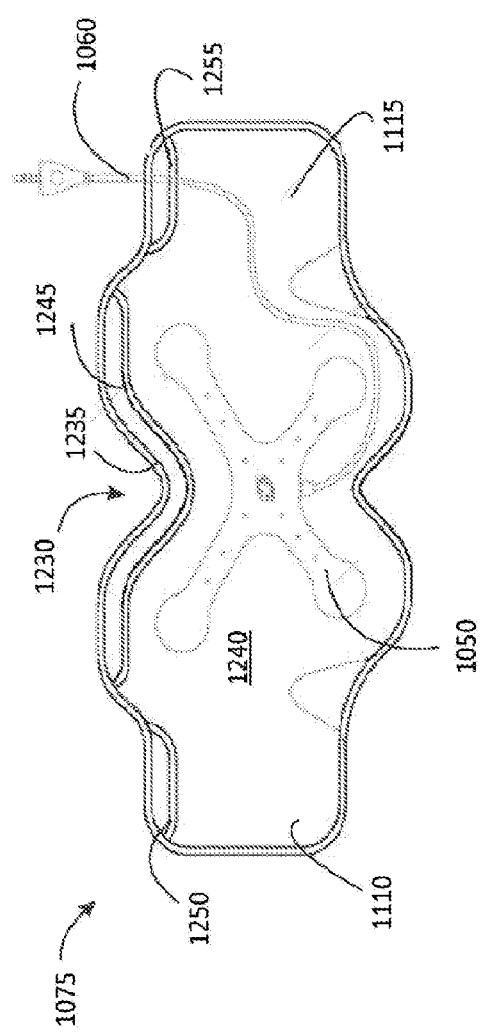

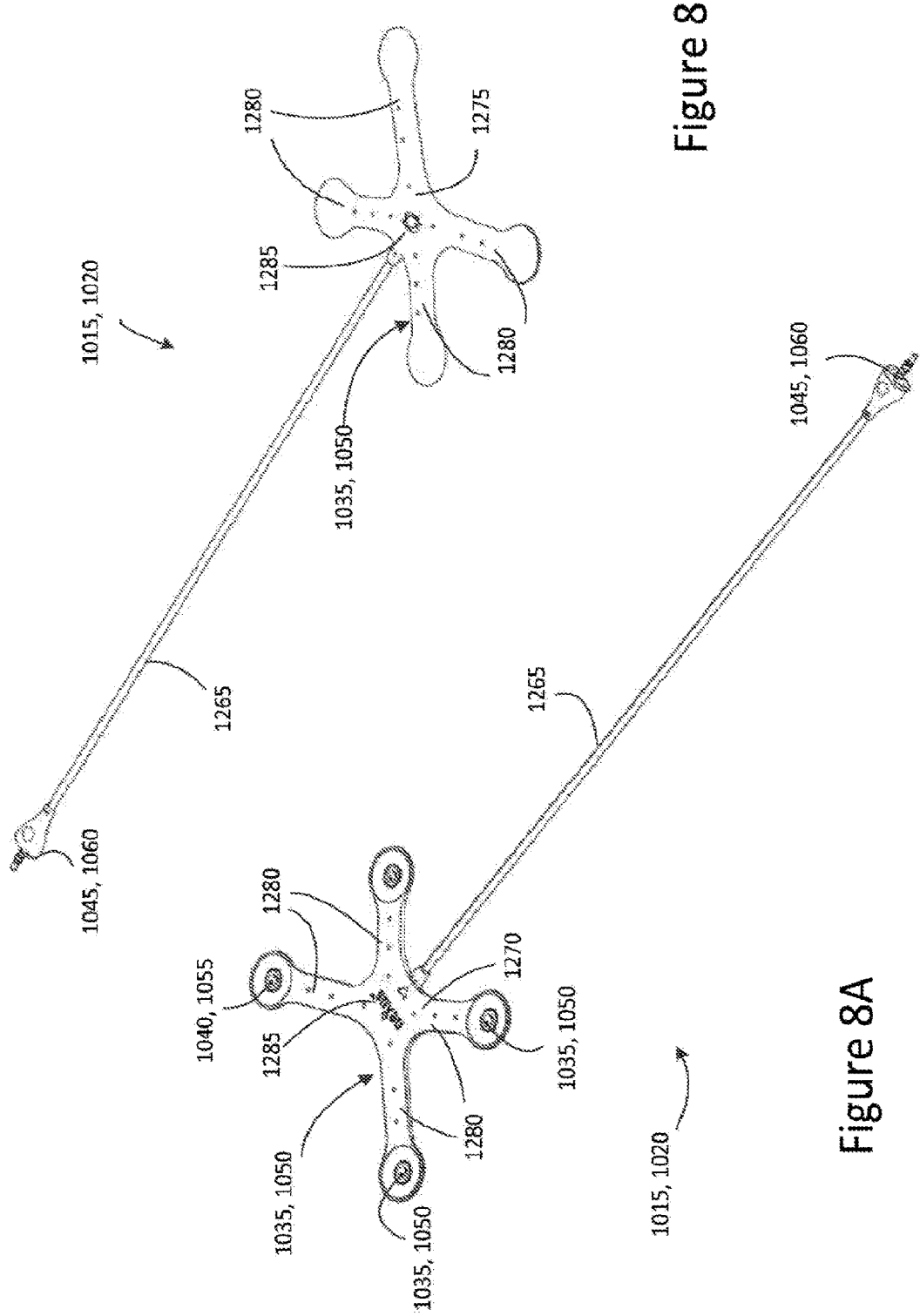

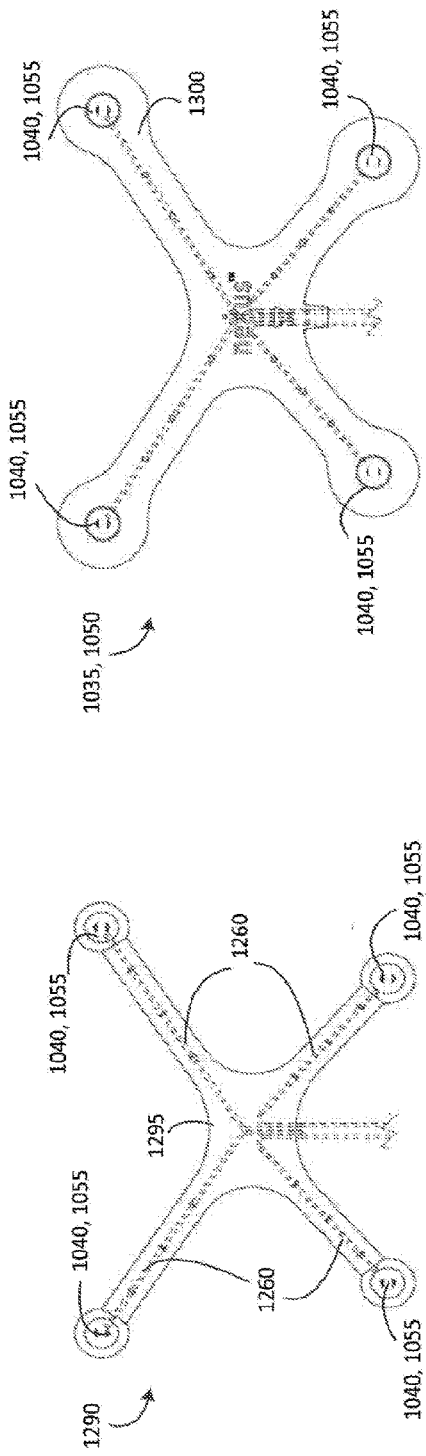
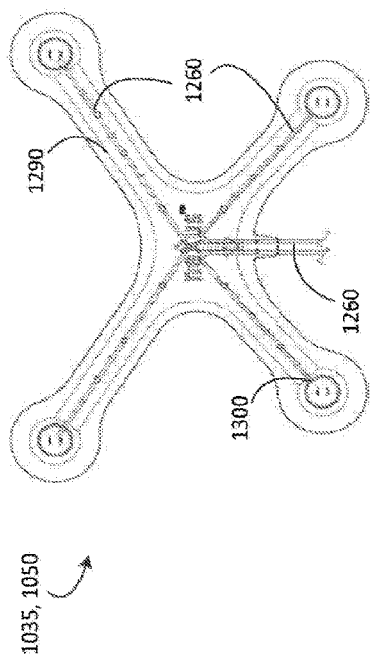
Figure 10
Figure 11
Figure 9

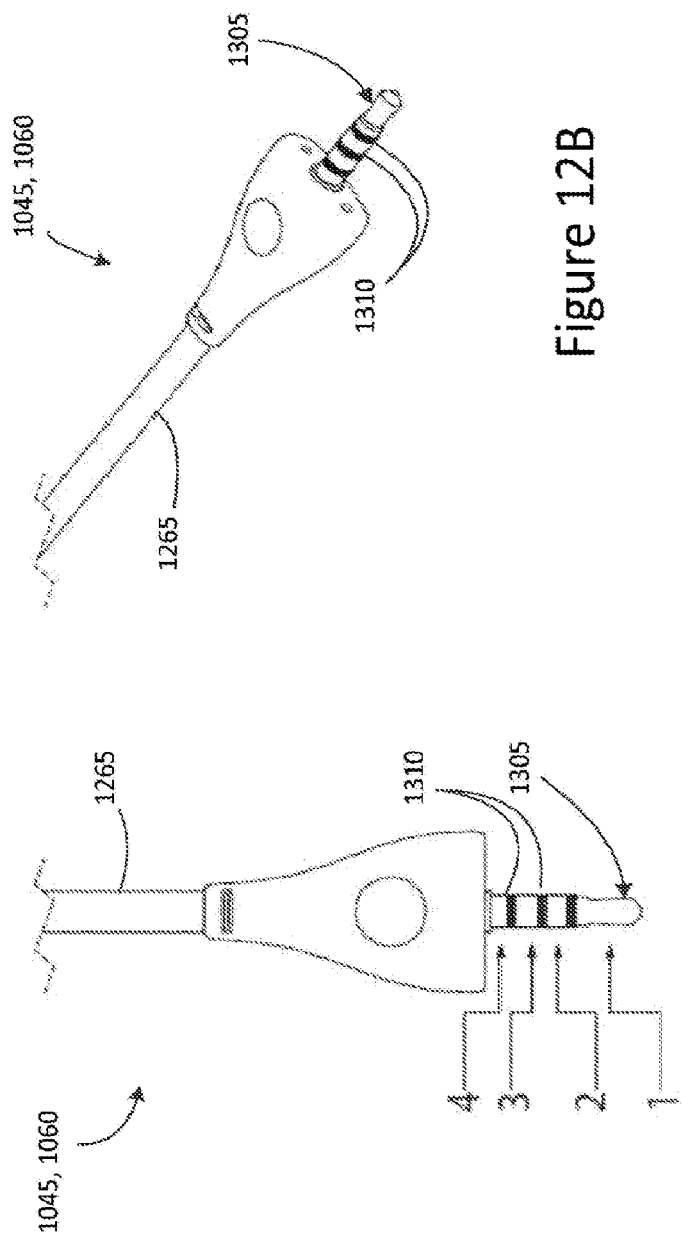

SYSTEM, DEVICE AND GARMENT FOR DELIVERING TRANSCUTANEOUS ELECTRICAL STIMULATION

CROSS REFERENCE TO RELATED APPLICATIONS

This application is a continuation of U.S. application Ser. No. 15/028,191, filed Apr. 8, 2016, now U.S. Pat. No. 9,962,544, which is the U.S. national phase of International Application No. PCT/AU2014/000968 filed on Oct. 10, 2014, and claims priority to Australian Patent Application Nos. 2013903922 and 2013903926, both filed on Oct. 11, 2013, the disclosures of which are all hereby incorporated herein by reference in their entirety.

TECHNICAL FIELD

Described embodiments generally relate to systems, devices, assemblies and garments for delivering transcutaneous electrical stimulation. Such embodiments may be employed to deliver electrical stimulation in the treatment of a waste evacuation dysfunction such as a faecal waste evacuation dysfunction, for example.

BACKGROUND

Dysfunction in waste evacuation from the gastrointestinal tract can take various forms. For example intestinal incontinence or constipation can occur. Treatment systems exist for treating constipation by providing electrical stimulus via subcutaneously implanted electrodes positioned around the lower bowel. Electrical stimulation provided using such electrodes can be used to sequentially activate muscle fibres around the bowel to force a peristaltic action to occur. However, such treatment systems are undesirably invasive. Further, while such systems may have an immediate effect in the system to evacuate the bowel, they do not necessarily address the cause of the constipation. Additionally, such systems do not appear to have much or any effect beyond the immediate time of electrical stimulation.

Intractable constipation and soiling are common in various communities, effecting both young and old people alike. Available treatments are generally uncomfortable, can cause social distress for those afflicted and can be a significant drain on the healthcare system. Individuals that suffer from constipation may also have psychological issues. Constipation may also be a side effect of some kinds of medication, such as opiates. Most laxative therapies are designed to either soften the stool or stimulate the bowel by chemicals in the gastrointestinal lumen. Patients with chronic constipation or intractable constipation may have failed other treatment methods, including pharmaceutical treatments. Further, patients on therapies for other diseases or conditions in which constipation is a side effect of such therapies may not be able to be co-administered pharmaceutical treatments for that constipation.

International Patent Publication No. WO 2012/116407 is directed towards a method of treating a waste evacuation dysfunction comprising administering transcutaneous electrical stimulation (TES) to at least one lower pelvic and/or sacral region for specific treatment regimens. In particular, WO 2012/116407 discusses fixing a plurality of electrodes to an apparatus such as a belt to aid in the positioning of electrodes to a lumbar and/or lower front abdominal area of a patient and to aid in the positioning of the spacing of the electrodes. A stimulation device is employed to transmit TES to the electrodes, and thus to deliver TES to the patient wearing the apparatus.

It is desired to address or ameliorate one or more shortcomings or disadvantages associated with prior fecal waste evacuation treatment systems, devices or methods, or to a least provide a useful alternative thereto.

SUMMARY

Some embodiments relate to an electrode connector assembly for use in transcutaneous electrical stimulation, comprising a flexible web extending in a plane; first, second, third and fourth electrode connectors carried by the web and spaced from each other about the web in the plane; an electrical connector; and first, second, third and fourth conductors electrically coupling the respective first, second, third and fourth electrode connectors to the electrical connector.

In some embodiments, the first, second, third and fourth electrode connectors may each comprise a snap connector component.

In some embodiments, the first, second, third and fourth electrode connectors may each comprise one of a male snap connection component and female snap connection component.

In some embodiments, the web may comprise a conductor support structure to support the first, second, third and fourth conductors and an encasing material encasing at least part of each of the first, second, third and fourth conductors and at least partially encasing the conductor support structure.

In some embodiments, the encasing material may fully encase the support structure but only partially encase each of the first, second, third and fourth electrode connectors.

In some embodiments, the web may be shaped to define respective vertices of a quadrilateral shape, with the first, second, third and fourth electrical connectors positioned at respective vertices of the quadrilateral shape. In some embodiments, the quadrilateral shape may be a trapezoid. In some embodiments, the web may have a first face that is generally planar and an opposite second face. In some embodiments, the second face may comprise at least one curved surface.

In some embodiments, the assembly may further comprise a flexible cable interconnection the electrical connector and the web, the cable enclosing a length of each of the first, second, third and fourth conductors. In some embodiments, the electrical connector may comprise a four-pole jack or a four pin port plug to electrically couple the assembly to a stimulation generation device.

In some embodiments, the web may comprise a central hub portion and a plurality of outer portions extending from the hub portion. In some embodiments, at least one of the first, second, third and fourth conductors may pass through the central hub. In some embodiments, the plurality of outer portions may house the first, second, third and fourth electrode connectors. In some embodiments, the web may be approximately X-shaped. In some embodiments, the web may be approximately quadrilateral-shaped. In some embodiments, the cable may be integrally formed with the web.

Some embodiments relate to an electrode connector assembly for use in transcutaneous electrical stimulation, comprising: a first pair of electrode connectors; a second pair of electrode connectors; and a flexible substrate carrying the first and second pairs of connectors in spaced relation to each other; a plurality of conductors carried by the substrate and arranged to electrically separately couple each connector of each of the first and second pairs of electrode connectors to a current stimulation device via an electrical connector.

Some embodiments relate to an electrical stimulation system comprising: an electrical stimulation generation device; and at least one electrode connector assembly as described above to electrically couple to and receive electrical potential from, the electrical stimulation generation device via the electrical connector.

In some embodiments, the at least one electrode connector assembly may comprise two electrode connector assemblies.

In some embodiments, the system may further comprise a plurality of electrodes to be positioned on skin and to electrically couple to respective first, second third and fourth electrode connectors.

In some embodiments, the system may further comprise a wearable garment to carry the at least one electrode connector assembly.

Some embodiments relate to a garment to be worn around a waist of a person to facilitate transcutaneous electrical stimulation of the person, the garment comprising: a first part to receive a first electrode connector assembly, wherein the first part comprises a plurality of electrode connectors to electrically couple to respective mating connectors of the first electrode connector assembly; and a second part to receive a second electrode connector assembly, wherein the second part comprises a plurality of electrode connectors to electrically couple to respective mating connectors of the second electrode connector assembly; wherein the first part and the second part are arranged to be coupled together when worn by the person.

In some embodiments, the first part may comprise a body portion and first and second ends and the second part may comprise a body portion and first and second ends and wherein the first and second ends of the first part may be respectively connected to the first and second ends of the second part. In some embodiments, the first and second ends of the first part may be elongated belt portions extending from the body portion.

In some embodiments, the first and second parts may be detachably coupled together. In some embodiments, the first end of the first part may be detachably coupled to the first end of the second part. In some embodiments, the second end of the first part may be detachably coupled to the second end of the second part. In some embodiments, the garment may further comprise at least one garment fastening portion to couple the first part and the second part together about the person.

In some embodiments, the plurality of electrode connectors of the first part may be disposed on the body portion of the first part and the plurality of electrode connectors of the second part may be disposed on the body portion of the second part.

In some embodiments, the plurality of electrode connectors of the first and second parts may extend from a major surface of the body portions of the first and second parts, respectively, to a reverse surface of the body portions of the first and second parts, respectively.

In some embodiments, the garment may further comprise a first pocket provided on the reverse surface of the body portion of first part, wherein the first pocket may be arranged to receive the first electrode assembly via a first pocket opening.

In some embodiments, the first pocket may extend along a length of the first part towards the first and second ends and include at least one first side pocket to accommodate an electrical connector of the first electrode connector assembly.

In some embodiments, the garment further comprises a second pocket provided on the reverse surface of the body portion of second part, wherein the second pocket may be arranged to receive the second electrode assembly via a second pocket opening.

In some embodiments, the second pocket may extend along a length of the second part towards the first and second ends and include at least one second side pocket to accommodate an electrical connector of the second electrode connector assembly.

In some embodiments, the first part of the garment may include an alignment tab for aligning the first part with a spine of a person to assist in the placement of the garment on the person.

In some embodiments, the second part of the garment may include an alignment tab for aligning the second part with a naval of a person to assist in the placement of the garment on the person.

In some embodiments, the garment further comprises a measurement indicator disposed along a length of the first and/or second end of the first part and arranged to cooperate with a measurement marker disposed on the first and/or second end of the second part to assist with selecting a suitable waist size for the garment.

In some embodiments, each of the plurality of electrode connectors is associated with at least one location indicator disposed on the body portions of the first and second parts of the garment, wherein each of the plurality of location indicators is arranged to identify a suitable location for affixing an electrode pad to the associated electrode connector.

In some embodiments, the garment further may comprise a pocket arranged to receive a stimulation generation device.

In some embodiments, at least a portion of the garment may be composed of a stretchable material. In some embodiments, at least the ends of the first and second parts of the garment may be composed of a stretchable material and the body portions of the first and second parts may be composed of a non-stretchable material. In some embodiments, the garment may be composed of at least one of a flexible material, a breathable material and a washable material.

Some embodiments relate to an apparatus for use in transcutaneous electrical stimulation comprising a garment as described above and a first and second electrode connector assembly as described above, wherein the plurality of electrode connectors of the first part of the garment are electrically coupled to respective mating connectors of the first electrode connector assembly and the plurality of electrode connectors of the second part of the garment are electrically coupled to respective mating connectors of the second electrode connector assembly.

In some embodiments, the apparatus may further comprise an electrical stimulation generation device arranged to transmit transcutaneous electrical stimulation to the first and second electrode connector assemblies.

Some embodiments relate to a use of the apparatus as described above to transmit transcutaneous electrical stimulation to a patient wearing the garment for treating a waste evacuation dysfunction. Some embodiments relate to a use of the apparatus as described above to transmit transcutaneous electrical stimulation to a patient wearing the garment for treating a waste evacuation dysfunction related to the gastrointestinal tract.

Some embodiments relate to a method of treating waste evacuation dysfunction by delivering transcutaneous electrical stimulation to a patient, the method comprising: providing the garment as described above, including the first and second electrode connector assembly, as described above, about a waist of the patient, connecting the electrical connectors of the first and second electrode connector assemblies to a stimulation generation device; and activating the stimulation generation device to administer transcutaneous electrical stimulation to the patient via the first and second electrode connector assemblies provided in the garment.

In some embodiments, the transcutaneous electrical stimulation is administered to a lumbar area or sacral region of the patient via the first electrode connector assembly and transcutaneous electrical stimulation is administered to a lower front abdominal or pelvic area of the patient via the first electrode connector assembly.

Some embodiments relate to an electrical stimulation kit comprising a garment as described above and a first and second electrode connector assembly as described above, wherein the garment is arranged to receive the first and second electrode connector assemblies and the first and second electrode connector assemblies are arranged to connect to an electrical stimulation generation device. In some embodiments, the electrical stimulation kit further comprises the electrical stimulation generation device.

Some embodiments relate to a method of treating waste evacuation dysfunction such as faecal waste evacuation dysfunction by delivering transcutaneous electrical stimulation to a patient, the method comprising transmitting transcutaneous electrical stimulation to a first and second electrode connector assembly, as described above, provided in a garment, as described above, the garment being worn about a waist of the patient.

In some embodiments, the transcutaneous electrical stimulation may comprise a stimulation current of magnitude less than about 40 mA and greater than zero. In some embodiments, the current may be provided at a carrier frequency of between about 1 kHz and about 10 kHz, with a modulated frequency of about 20 to about 300 Hz. In some embodiments, the current may be provided at a carrier frequency of about 4 kHz and the modulated frequency may be about 80 Hz to 150 Hz. In some embodiments, the electrical stimulation may comprise interferential electrical current stimulation.

In some embodiments, the method further comprises providing transcutaneous electrical stimulation to the first and/or second second electrode connector assembly for at least one treatment period per day over a treatment term of at least one week. In some embodiments, the method further comprises providing transcutaneous electrical stimulation for two or three treatment periods per day. In some embodiments, the treatment period is between about 10 minutes and about 90 minutes. In some embodiments, the treatment period is between about 20 minutes and about 60 minutes.

BRIEF DESCRIPTION OF THE DRAWINGS

Embodiments are described in further detail below, by way of example, with reference to the accompanying drawings, in which:

FIGS. 5A, 5B and 5C are front, side and rear views of a pocket to be worn with the garment and to carry a stimulation device;

FIG. 6A is an illustration of one side of a first part of the garment;

FIG. 6B is an illustration of an opposite side of the first part of the garment;

FIG. 7A is an illustration of one side of a second part of the garment;

FIG. 7B is an illustration of an opposite side of the second part of the garment;

FIG. 8A is a perspective view showing an underside of an electrode connector assembly according to some embodiments;

FIG. 8B is a perspective view of an upper side of the electrode connector assembly;

FIG. 9 is a schematic illustration of a support frame used to support conductors in the electrode connector assembly;

FIG. 10 is a schematic illustration of a substrate or flexible web of the electrode connector assembly;

FIG. 11 is a schematic illustration of the substrate or flexible web, showing the location and position of the frame within the web;

FIG. 12A is an illustration of a connector jack at one end of the electrode connector assembly;

FIG. 12B is a perspective view of the connector jack of FIG. 12A;

DETAILED DESCRIPTION

Described embodiments generally relate to systems, devices, assemblies and garments for delivering transcutaneous electrical stimulation. Such embodiments may be employed to deliver electrical stimulation in the treatment of a waste evacuation dysfunction, for example.

As noted in the background above, WO 2012/116407 is concerned with delivering transcutaneous electrical stimulation to a patient and discusses the fixing of electrodes to lumbar and/or lower front abdominal areas of patients on regions. However, WO 2012/116407 does not envisage or anticipate problems associated with placement of the electrodes on individuals of different body shapes or changes in an individual's body shape due to associated movement i.e., as the person moves between a standing position and a sitting position. Some embodiments address or ameliorate some or all of these problems as discussed below. Other issues relating to ease and comfort of assembly and use of the transcutaneous stimulation system may be addressed by various features of the described embodiments.

Figure 1:
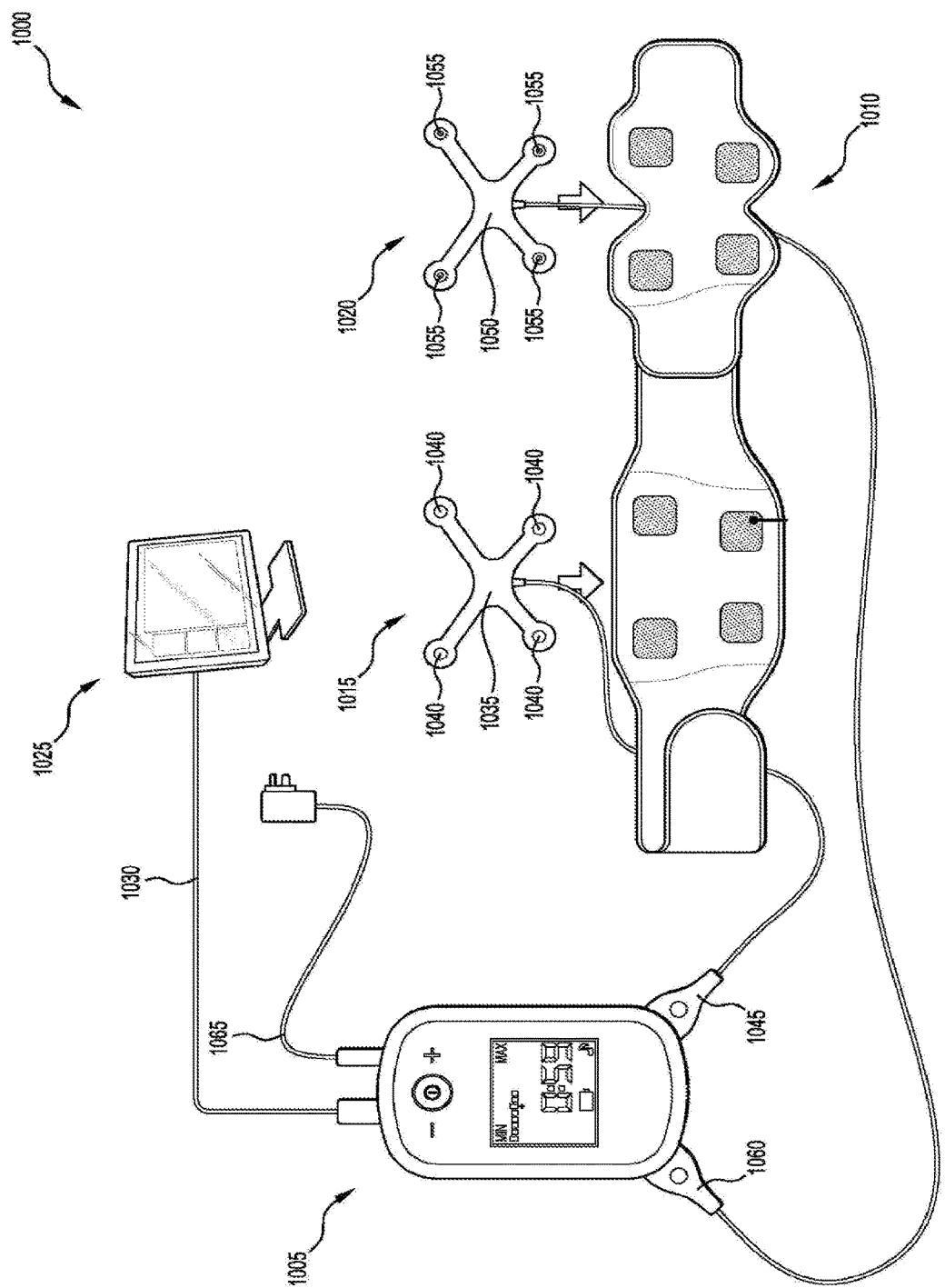
FIG. 1 is a schematic diagram of a transcutaneous electrical stimulation system.

Referring to FIG. 1, there is illustrated a stimulation system 1000 according to some embodiments. The stimulation system 1000 comprises a stimulation generation device 1005 arranged to deliver transcutaneous electrical stimulation to a patient wearing a garment 1010 by transmitting transcutaneous electrical stimulation to a first electrode connector assembly 1015 housed or mounted to the garment 1010. In some embodiments, the stimulation generation device 1005 is further arranged to deliver transcutaneous electrical stimulation to a second electrode connector assembly 1020 housed or mounted to the garment 1010.

International Patent Publication No. WO 2012/116407, the content of which is incorporated herein by reference, discusses various methods and regimes for treating a waste evacuation dysfunction by administering transcutaneous electrical stimulation (TES) to a patient. In some embodiments, the stimulation generation device 1005 of the stimulation system 1000 is configured to generate and transmit transcutaneous electrical stimulation in accordance with the teachings of WO 2012/116407 to treat a waste evacuation dysfunction. For example, the stimulation generation device 1005 may be configured to provide a stimulation current of magnitude less than about 40 mA and greater than zero. The current may be provided at a carrier frequency of between about 1 kHz and about 10 kHz, with a modulated frequency of about 20 to about 300 Hz. Alternatively, the carrier frequency may be about 4 kHz and the modulated frequency is about 80 Hz to 150 Hz. Furthermore, the electrical stimulation may comprise interferential electrical current stimulation.

In some embodiments, the stimulation generation device 1005 may be configured to provide transcutaneous electrical stimulation to the first and/or second second electrode connector assembly 1015, 1020 for at least one treatment period per day over a treatment term of at least one week, and/or for two or three treatment periods per day. In some embodiments the treatment period may be between about 10 minutes and about 90 minutes, or between about 20 minutes and about 60 minutes.

The stimulation generation device 1005 may be arranged to communicate with a computing device 1025, for example, via a cable 1030 such as a USB cable. However, in other embodiments, the stimulation generation device 1005 may communicate with the computing device 1025 via a telecommunications network, such as a WiFi network, Bluetooth, or the Internet. In some embodiments, the stimulation generation device 1005 communicates with the computing device 1025 to upload or download data associated with transcutaneous electrical stimulation being generated by the stimulation generation device 1005. For example, such data may include a log of transcutaneous electrical stimulation transmitted to a given patient for a particular duration of time or treatment period, or may include instructions for transmitting transcutaneous electrical stimulation to a given patient for a particular duration of time or treatment period.

The first electrode connector assembly 1015 may include a first substrate 1035 carrying a plurality of electrode connectors 1040 electrically coupled to an electrical connector 1045. The electrical connector 1045 may be arranged to connect to the stimulation generation device 1005 to thereby enable the transmission of transcutaneous electrical stimulation from the stimulation generation device 1005 to the plurality of electrode connectors 1040.

The second electrode connector assembly 1020 may include a second substrate 1050 carrying a plurality of electrode connectors 1055 electrically coupled to an electrical connector 1060. The electrical connector 1060 may be arranged to connect to the stimulation generation device 1005 to thereby enable the transmission of transcutaneous electrical stimulation from the stimulation generation device 1005 to the plurality of electrode connectors 1055.

In some embodiments, the stimulation generation device 1005 may be arranged to receive a power cable 1065 to enable the stimulation generation device 1005 to be connected to a power source (not shown).

Figure 2:
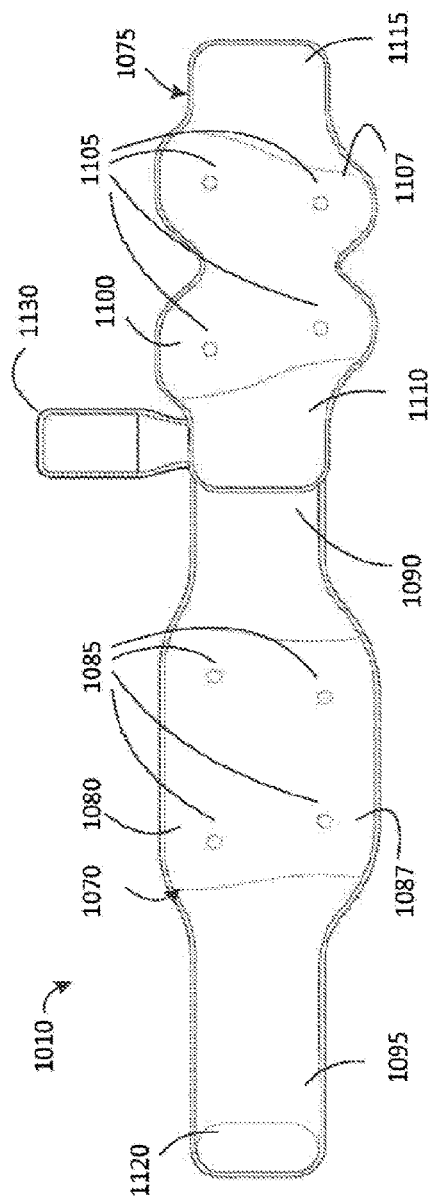
FIG. 2 is an illustration of a garment usable as part of the system of FIG. 1, showing the garment in a fully open position.

Referring to FIG. 2, there is depicted a top view of the garment 1010. The garment 1010 comprises a first part 1070 arranged to receive the first substrate 1035 and a second part 1075 arranged to receive the second substrate 1050. In some embodiments, the garment 1010 is a two-piece belt.

The first part 1070 comprises a first or major surface 1080 having a plurality of electrode connectors 1085 disposed thereon. The electrode connectors 1085 are configured to electrically couple to respective mating electrode connectors 1040 of the first substrate 1035 of the electrode connector assembly 1015. The first part 1070 further comprises a body portion 1087, a first end 1090 and a second end 1095. In some embodiments, the plurality of electrode connectors 1085 is disposed on the body portion 1087 of the first part 1070. In some embodiments, the first and second ends 1090, 1095, may be elongated belt parts extending from the body portion 1087.

The second part 1075 comprises a first or major surface 1100 having a plurality of electrode connectors 1105 disposed thereon and configured to electrically couple to respective mating electrode connectors 1055 of the second substrate 1050 of the first electrode connector assembly 1020. The second part 1075 further comprises a body portion 1107, a first end 1110 and a second end 1115. In some embodiments, the plurality of electrode connectors 1105 is disposed on the body portion 1107 of the second part 1075.

The first and second ends 1090 and 1095 of the first part 1070 may be arranged to connect or fasten to the first and second ends 1110 and 1115 of the second part, respectively. In some embodiments, the first ends 1090 and 1110 and/or the second ends 1095 and 1115 are fixedly fastened or secured together. In other embodiments, the first ends 1090 and 1110 and/or the second ends 1095 and 1115 are detachably connectable to one another, for example, by means of a hook and loop fastener, such as Velcro, or a hook and eye fastener.

In some embodiments, as depicted in FIG. 2, the first part 1070 includes a fastening portion 1120, such as a hook fastener, for example, Velcro, disposed on the major surface 1080 toward the second end 1095, and may be arranged to engage with a reverse or opposed second surface 1125 (FIG. 3) of the second part 1075 toward the second end 1115. For example, a corresponding fastening portion (not shown) may be disposed on the reverse surface 1125 of the second part 1075. In some embodiments, the second end 1115 of the reverse surface 1125 of the second part 1075 may be composed of a looped fabric or may have disposed thereon a strip of looped fabric arranged to engage with the fastening portion 1120.

Figure 4:
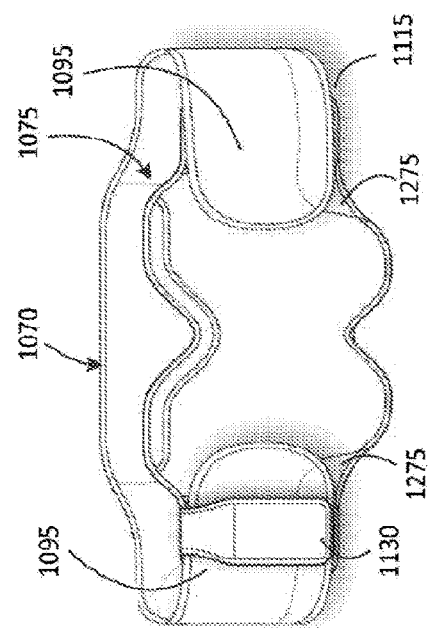
FIG. 4 is an illustration of the garment, showing the garment in a closed position in which it can be worn by the patient.
Figure 3:
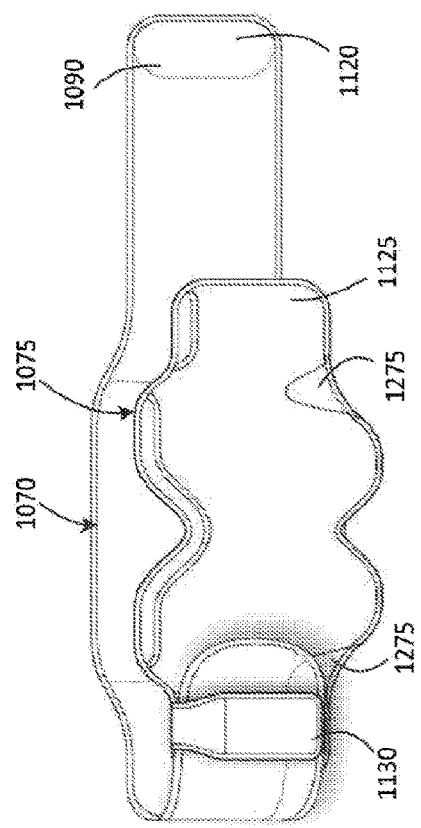
FIG. 3 is an illustration of the garment of FIG. 2, shown in a position ready to be affixed to a patient.

FIG. 3 depicts a perspective view of the garment 1010 wherein the second ends 1095 and 1115 of the first and second parts, 1070 and 1075, respectively, are engaged or connected to one another and the first ends 1090 and 1110 of the first and second parts, 1070 and 1075, respectively, are disengaged or disconnected from one another such that the garment 1010 is in an open configuration or position for affixing to a person. FIG. 4 depicts a perspective view of the garment 1010 wherein both the first ends 1090 and 1110 and the second ends 1095 and 1115 of the first and second parts, 1070 and 1075 respectively, are engaged or connected to one another, such that the garment 1010 is in a closed configuration or position in which it can be worn by a person.

As depicted in FIGS. 2, 3, and 4, the garment may include a pocket 1130 for receiving the stimulation generation device 1005. In some embodiments, and as depicted in FIG. 2, the pocket 1130 is disposed at or toward the first end 1090, 1110 of the first and second parts 1070, 1075, respectively, as may be more convenient for a left-handed person. In other embodiments, and as depicted in FIGS. 3 and 4, the pocket 1130 is disposed at or toward the second ends 1095, 1115 of the first and second parts 1070, 1075, respectively, as may be more convenient for a right-handed person. In some embodiments, the pocket 1130 is fixedly attached to the garment 1010. In other embodiments, the pocket 1130 is detachably connected to the garment 1010, for example, by means of a hook and loop fastener, for example, Velcro, or a hook and eye fastener, or a loop arranged to slidably receive the first or second ends 1090, 1095, of the first part 1070 and/or first or second ends 1110, 1115, of the second part 1075.

FIGS. 5A, 5B, and 5C are front, side and rear views of a pocket 1130 according to one embodiment. As illustrated in FIG. 5A, the pocket 1130 comprises a sleeve portion 1135 arranged to receive the stimulation generation device 1005 through an opening 1140 disposed on a major or first surface 1145 of the pocket 1130.

Referring to FIG. 5C, the pocket 1130 includes a first fastening portion 1150 disposed on or toward an upper section 1155 of a reverse or second opposed surface 1160 of the pocket 1130. The first fastening portion 1150 is arranged to engage with or fasten to the major surface 1080, 1110 of the first or second parts 1070, 1075, respectively. Thus, in use, the upper section 1155 is arranged to bend or fold about a lateral axis A-A of the pocket 1130 to thereby sandwich the first and/or second parts 1070, 1075 of the garment 1010 between the upper section 1155 and a lower section 1165 of the reverse surface 1160 of the pocket 1130.

In some embodiments, the first fastening portion 1150 is arranged to engage with or fasten to a corresponding fastening portion (not shown) provided on the major surface 1080, 1110. In other embodiments, the major surface 1080, 1110 is composed of a material suitable for engaging with or fastening to the fastening portion 1150. For example, the fastening portion 1150, and/or fastening portion (not shown) provided on the major surface 1080, 1110, and/or the major surface 1080, 1110 may be composed of a hook and/or loop type fabric, for example, Velcro.

In some embodiments, the pocket 1130 includes a second fastening portion 1170 disposed on or toward the lower section 1165 of the reverse surface 1160 of the pocket 1130. The second fastening portion 1170 is arranged to engage with or fasten to a second opposed or reverse surface 1175 (FIG. 6B) of the first part 1070 of the garment 1010. In some embodiments, the second fastening portion 1170 is arranged to engage with or fasten to a fastening portion (not shown) provided on the reverse surface 1175 (FIG. 6B) of the first part 1070. In other embodiments, the reverse surface 1175 of the second part 1075 is composed of a material suitable for engaging with or fastening to the fastening portion 1170. For example, the fastening portion 1170, and/or fastening portion (not shown) provided on the reverse surface 1175, and/or the reverse surface 1175 of the first part 1070 may be composed of a hook and/or loop type fabric, for example, Velcro. In some embodiments, the second fastening portion 1170 may be arranged to engage with or fasten to the second opposed or reverse surface 1125 of the second part 1075 of the garment 1010.

In some embodiments, the pocket 1130 includes a third fastening portion 1177 disposed towards the upper section 1155 of the opposed surface 1160 of the pocket 1130. The third fastening portion 1177 may be arranged to capture and manage flexible cables 1265 (FIGS. 8A and 8B) interconnecting the electrical connectors 1045, 1060 and the substrates 1035, 1050, respectively. In other embodiments, the pocket 1130 includes only the first fastening portion 1150 and the second fastening portion 1170.

In some embodiments, the first fastening portion 1150 extends from the upper section 1155 towards the lower section 1165 of the reverse surface 1160 such that in use, the first fastening portion 1150 disposed on the upper section 1155 is arranged to engage with the major surface 1080, 1110 of the first or second parts 1070, 1075, respectively and the first fastening portion disposed on the lower section 1165 is arranged to engage with the reverse surface 1175, 1125 of the first or second parts 1070, 1075, respectively.

Referring now to FIG. 6A, there is illustrated a detailed top view of the first or major surface 1080 of the first part 1070 of the garment 1010. As depicted, the electrode connectors 1085 are disposed on the major surface 1080 of the first part 1070 in a spaced-apart manner.

In some embodiments, each electrode connector 1085 is associated with at least one location indicator 1180 disposed on the major surface 1080 for identifying a preferable or suggested location for the positioning of an electrode pad (not shown). The electrode pad is arranged to make contact with a user's skin and suitable positioning of the electrode pads at the location indicator 1180 of the garment 1010 ensures or assists in an efficient transmission of transcutaneous electrical stimulation from the electrode connectors 1085 to the electrode pads, and therefore, to the user wearing the a garment 1010. In some embodiments and as illustrated in FIG. 5A, each electrode connector 1085 is associated with a plurality of location indicators 1180, for example, in the form of markings provided on the major surface 1080, to identify various suitable locations for the positioning of the electrode pad (not shown). For example, the plurality of location indicators 1180 may identify a positioning for the electrode pads for small, medium and large sized patients, to thereby facilitate or accommodate for persons of varying sizes. In some embodiments, the electrode pads are adhesive pads, such as UltraStim® Pad Electrodes, as produced by AXELGAARD Manufacturing Co., Ltd, and may be easily replaceable.

In some embodiments, the garment 1010 includes a measurement indicator 1185 disposed along the major surface 1080 of the first and/or second ends 1090 and 1095. The measurement indicator 1185 serves to assist in selecting and adjusting the garment to a suitable size for a given patient.

As illustrated in FIG. 6A, the garment 1010 may include an alignment tab 1190 disposed on an upper central section 1195 of major surface 1080 of the first part 1070 to assist in aligning the first part 1070 of the garment 1010 with a patient's spine. In some embodiments, by aligning the alignment tab 1190 with the patient's spine, the garment 1010 may be suitably placed on a patient to achieve efficient and effective transmission of transcutaneous electrical stimulation to the patient.

Referring now to FIG. 6B, there is illustrated a detailed top view of the reverse or second opposed surface 1175 of first part 1070 of the garment 1010. As depicted, the first part 1070 of the garment 1010 comprises a pocket 1200 arranged to receive the substrate 1035 via a first pocket opening 1205 provided toward the upper central section 1195.

In some embodiments, the pocket 1200 extends along a length of the first part 1070 toward the first and second ends, 1090, 1095. A second pocket opening 1210 may be disposed toward the first end 1090 and/or a third pocket opening 1215 may be disposed toward the second end 1095. The second pocket opening 1210 and/or the third pocket opening 1215 may be employed to allow the electrical connector 1045 connected to the substrate 1035 to exit the pocket 1200 for connection to the stimulation generation device 1005. In some embodiments, the second and/or third pocket openings 1210, 1215, may include a plurality of pocket opening sections (not shown) to provide a plurality of exits for the electrical connector 1045 so that a suitable exit may be selected depending on a waist measurement of the patient.

In some embodiments, the electrode connectors 1085 disposed on the major surface 1080 extend from the major surface 1080 through the first part 1070 to the reverse surface 1175 such that they are accessible from within the pocket 1200. Thus, when the electrode conductor assembly 1015 is positioned within the pocket 1200, the electrode connectors 1040 of the substrate 1035 may engage or mate with the respective electrode connectors 1085. In some embodiments, the electrode connectors 1085 each comprise a snap connector component (not shown) arranged to engage or connect to a corresponding snap connector component (not shown) provided on respective mating connectors 1040 of the first substrate 1035 of the first electrode connector assembly 1015. The snap connector components (not shown) may be one of male or female snap connector components. In some embodiments, the electrode connectors 1085 and respective mating connectors 1040 may be colour coded to assist with correct attachment of the electrode connectors 1085 to the respective mating connectors 1040.

Referring now to FIG. 7A, there is illustrated a detailed top view of the major surface 1100 of the second part 1075 of the garment 1010. As depicted, the electrode connectors 1105 are disposed on the major surface 1100 of the second part 1075 in a spaced-apart manner.

In some embodiments, each electrode connector 1105 is associated with at least one location indicator 1220 disposed on the major surface 1100 for identifying a preferable or suggested location for the positioning of an electrode pad (not shown) to ensure or assist in an efficient transmission of transcutaneous electrical stimulation from the electrode connectors 1085 to the electrode pads, and therefore, to a user wearing the garment 1010. In some embodiments and as illustrated in FIG. 7A, each electrode connector 1105 is associated with a plurality of location indicators 1220, for example, in the form of markings provided on the major surface 1100, to identify various suitable locations for the positioning of the electrode pad (not shown). For example, the plurality of location indicators 1220 may identify a positioning for the electrode pads for small, medium and large sized patients, to thereby facilitate or accommodate for persons of varying sizes. In some embodiments, the electrode pads are adhesive pads, such as UltraSam® Pad Electrodes, as produced by AXELGAARD Manufacturing Co., Ltd, and may be easily replaceable.

In some embodiments, the garment 1010 includes a measurement marker 1225 disposed toward the first and/or second ends 1110 and 1115 of the major surface 1100. The measurement marker 1225 may be arranged to cooperate with the measurement indicator 1185 to select a suitable sizing for the garment to be worn by the patient and so determine where the first part should be fastened to the second part. In some embodiments, the measurement marker is a measurement tab.

In some embodiments, the second part is configured or shaped to assist in a positioning of the garment on a patient relative to the patient's navel. For example, and as depicted in FIGS. 7A and 7B, the second part 1075 comprises an alignment tab in the form of a concave or indented section 1230 provided at an upper central section 1235 of the second part 1075 and which is arranged to accommodate the patients navel.

Referring now to FIG. 7B, there is illustrated a detailed top view of the reverse surface 1125 of second part 1075 of the garment 1010. As depicted, the second part 1075 of the garment 1010 comprises a pocket 1240 arranged to receive the substrate 1050 via a first pocket opening 1245 provided toward the upper central section 1235 on the reverse surface 1125 of the second part 1075.

In some embodiments, the pocket 1240 extends along a length of the second part 1075 toward the first and second ends, 1110, 1115. A second pocket opening 1250 may be disposed toward the first end 1110 and/or a third pocket opening 1255 may be disposed toward the second end 1115. The second pocket opening 1250 and/or the third pocket opening 1255 may be employed to allow the electrical connector 1060 connected to the substrate 1050 to exit the pocket 1240 for connection stimulation generation device 1005. In some embodiments, the second and/or third pocket openings 1250, 1255, may include a plurality of pocket opening sections (not shown) to provide a plurality of exits for the electrical connector 1060 so that a suitable exit may be selected depending on a waist measurement of the patient.

The electrode connectors 1105 disposed on the major surface 1110 extend from the major surface 1110 through the second part 1075 to the reverse surface 1125 such that they are accessible from within the pocket 1240. Thus, when the electrode conductor assembly 1020 is positioned within the pocket 1240, the electrode connectors 1055 of the substrate 1050 may engage or mate with the respective electrode connectors 1105. In some embodiments, the electrode connectors 1105 each comprise a snap connector component (not shown) arranged to engage or connect to a corresponding snap connector component (not shown) provided on respective mating connectors 1055 of the second substrate 1050 of the electrode connector assembly 1020. The snap connector components (not shown) may be one of male or female snap connector components. In some embodiments, the electrode connectors 1105 and respective mating connectors 1055 may be colour coded to assist with correct attachment of the electrode connectors 1105 to the respective mating connectors 1055.

In some embodiments, the garment 1010 is composed of a flexible material. For example, the garment 1010 may be composed of a stretchable material. In some embodiments, the garment 1010 may be stretchable in parts and non-stretchable in other parts. For example, the body portions 1087 and 1107 of the garment 1010 may be composed of a non-stretchable material and the ends 1090 and 1095 of the first part 1070 and/or the ends 1110 and 1115 of the second part 1075 may be composed of a stretchable material. In some embodiments, the garment 1010 includes flexible or stretch zones 1257 (FIGS. 3 and 4), such as may be provided at an intersection of the body portions 1087 and 1107 and the ends 1090, 1095 and 1110, 1115, respectively, and/or toward a lower section (not shown) of the garment 1010 to thereby accommodate for movement of the patient as they assume different positions, for example, as they move between a sitting and standing position. In some embodiments, the garment 1010 is composed of at least one of a breathable material, a washable material, a soft material and a comfortable material. In this way, the garment 1010 may be capable of flexing, adapting or stretching to accommodate for a range of movements of a patient wearing the garment, such as movement from a standing to a sitting position or gentle play activities, and may thereby prevent or at least mitigate such activities interfering with a delivery of treatment to the patient via the electrode connector assembly 1015, 1020 provided on or within the garment 1010.

FIG. 8A depicts a perspective view of an underside of an electrode connector assembly 1015, 1020 and FIG. 8B depicts a perspective view of an upper side of the electrode connector assembly 1015, 1020. The electrode connector assembly 1015, 1020 comprises a substrate 1035, 1050 with a plurality of electrode connectors 1040, 1055 disposed thereon. The electrode connector assembly 1015, 1020 further comprises an electrical connector 1045, 1060 electrically coupled to the plurality of electrode connectors 1040, 1055 and arranged to connect to the stimulation generation device 1005. In some embodiments, and as described below in connection with FIGS. 9 to 11, the plurality of electrical connectors 1045, 1060, are electrically coupled to the electrode connector 1040, 1055 by means of a respective plurality of electrical conductors 1260 (FIGS. 9, 10, and 11). In some embodiments, the electrode connectors 1040, 1055 and electrical conductors 1260 may be colour coded to assist with correct attachment of the electrode connectors 1040, 1055 to the respective electrical conductors 1260.

In some embodiments, the electrode connector assembly 1015, 1020 further comprises a flexible cable 1265 interconnecting the electrical connector 1045, 1060 and the substrate 1035, 1050. The flexible cable 1265 may be arranged to enclose a length of each of the plurality of conductors 1260. In some embodiments, the cable 1265 is integrally formed with the substrate 1035, 1050. In some embodiments, the flexible cable is available in a variety of lengths to accommodate for varying waist measurements, and for example, the flexible cable 1265 connecting electrical connector 1045 to the substrate 1035 may have a length which is a multiple of a length of the flexible cable 1265 connecting electrical connector 1060 to the substrate 1050.

As illustrated in FIGS. 8A and 8B, the substrate 1035, 1050 may be a substantially flexible web extending a plane. The substrate 1035, 1050 or web may comprise a generally planar first face 1270 and a second opposite face 1275. In some embodiments, the second opposite face 1275 comprises at least one curved surface (not shown).

In some embodiments, each of the plurality of electrode connectors 1040, 1055 may be disposed on or housed in a respective outer portion 1280 of the substrate, 1035, 1050 extending outwardly from, and in the same plane as a central hub portion 1285 of the substrate 1035, 1050.

For example, in some embodiments, the substrate 1035, 1050 may be arranged in a substantially star configuration with each of the outer portions 1270 being displaced from one another and extending in different directions to one another in the same plane. In some embodiments, the substrate 1035, 1050 or web may be configured or shaped to define respective vertices of a quadrilateral shape, for example, a trapezoid, with each of the plurality of electrode connectors 1040, 1055 positioned at respective vertices of the quadrilateral shape. In some embodiments, the substrate 1035, 1050 may be arranged in a substantially X-shaped configuration.

Referring to FIG. 9, there is depicted a schematic illustration of a support frame 1290 of the substrate 1035, 1050. The support frame 1290 may be employed to support the plurality of conductors 1260 in the electrode connector assembly 1015, 1020. In some embodiments, at least one of the plurality of conductors 1260 passes through a central hub portion 1295 of the support frame 1250 corresponding to the central hub portion 1285 of the substrate 1035, 1050.

In some embodiments, the support frame 1290 of the substrate 1035, 1050 is encased at least partially within an encasing material 1300 as illustrated in FIGS. 10 and 11. For example, the encasing material may be a molded elastomeric material. In some embodiments, the encasing material 1300 encases the support frame 1290 but only partially encases each of the plurality of electrode connectors 1040, 1055. In this way the plurality of electrode connectors 1040, 1055 may be exposed and capable of engaging or connecting to respective mating electrode connectors 1085, 1105 of the garment 1010.

Referring now to FIGS. 12A and 12B, there is depicted a top view and a perspective view of an electrical connector 1045, 1060 according to some embodiments. The electrical connector 1045, 1060 comprises a connector jack 1305 disposed at a distal end of the electrical connector 1045, 1060. In some embodiments, the connector jack 1305 is a multiple-pole jack and is arranged to electrically couple the plurality of electrical conductors 1260 of the electrode connector assembly 1015, 1020 to the stimulation generation device 1005. In some embodiments, the connector jack 1305 is a four-pole jack and each pole 1310 is associated with and arranged to electrically couple a respective electrical conductor 1260 of the electrode connector assembly 1015, 1020 to the stimulation generation device 1005. In some embodiments, the connector jack is arranged to connect to a corresponding port (not shown) of the stimulation generation device 1005 to thereby allow transcutaneous electrical stimulation to be delivered to the electrode connector assembly 1015, 1020.

Figure 13B:
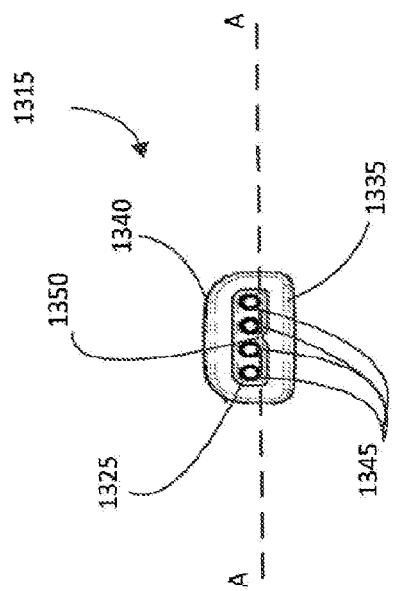
FIG. 13B is a side view of the connector plug of FIG. 13A.
Figure 13A:
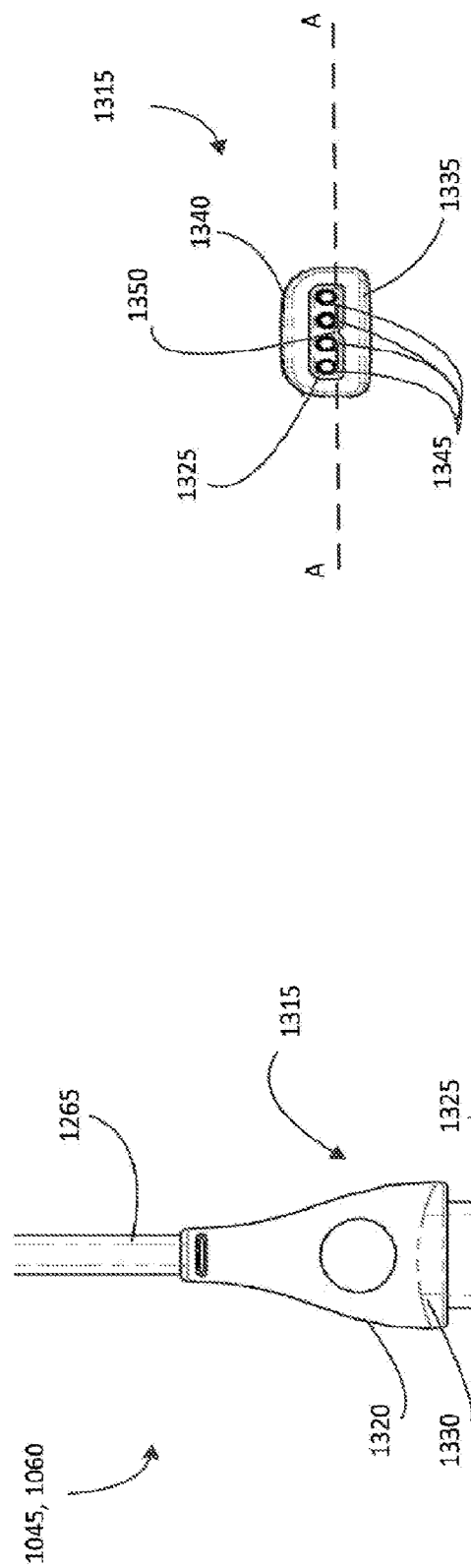
FIG. 13A is a top view of a connector plug at one end of the electrode connector assembly.
Figure 14:
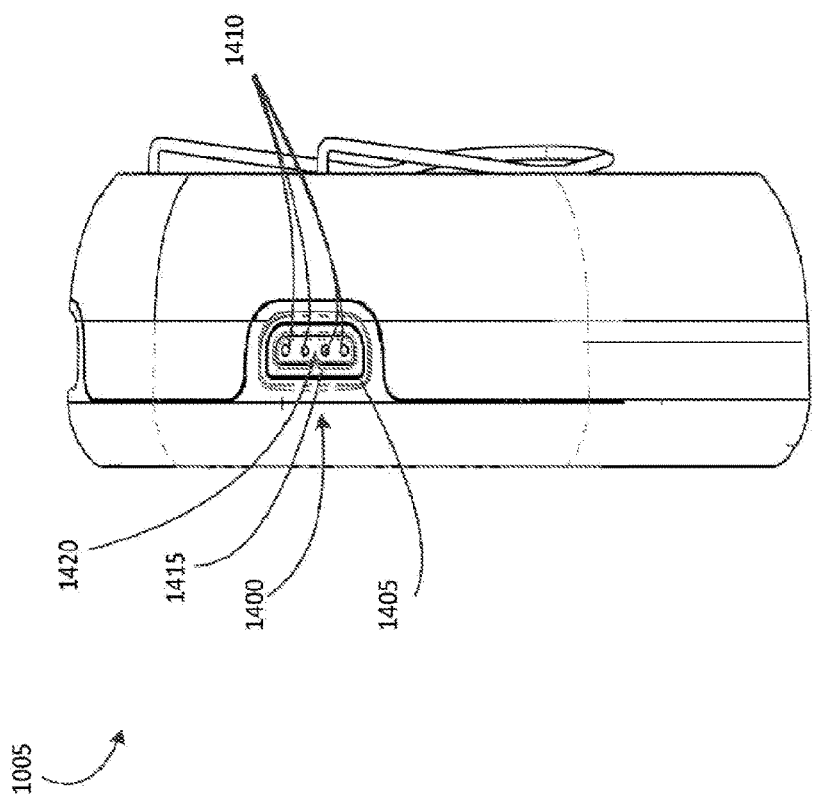
FIG. 14 is a side view of a stimulation generation device of the transcutaneous electrical stimulation system of FIG. 1 comprising a socket configured to cooperate with the connector plug of FIGS. 13A and 13B.

Referring to FIGS. 13A and 13B, there is a top view and a side view of an electrical connector 1045, 1060 for connecting to the support frame 1290 of the substrate 1035, 1050 according to some embodiments. The electrical connector 1045, 1060 comprises a connector plug 1315 and is arranged to electrically couple the plurality of electrical conductors 1260 of the electrode connector assembly 1015, 1020 to the stimulation generation device 1005, as depicted in FIG. 14. For example, in some embodiments, the stimulation generation device 1005 comprises a socket 1400 which is configured to cooperate with the connector plug 1315 to electrically couple the electrode connector assembly 1015, 1020 to the stimulation generation device 1005.

In some embodiments, the connector plug 1315 comprises a body portion 1320 and a projecting portion 1325 protruding from the body portion 1320. For example, the body portion 1320 may be a suitably shaped gripping portion.

In some embodiments, the body portion 1320 comprises a curved shoulder portion 1330 shaped to be received in a recessed portion 1405 of the socket 1400 of the stimulation generation device 1005. In some embodiments, the body portion 1320 comprises a substantially flat base portion 1335 and a rounded or curved surface portion 1340 and is configured to cooperate with a correspondingly shaped recessed portion 1405 of the socket 1400 of the stimulation generation device 1005. The socket 1400 may be recessed into a corner of the stimulation generation device 1005.

The projecting portion 1325 may include multiple pin ports 1345, such as four pin ports, and each pin port 1345 may be associated with and arranged to electrically couple to the electrical conductor 1260 of the electrode connector assembly 1015, 1020. Each pin port 1345 may be a separate electrically isolated signal channel. For example, the connector plug 1315 may have 2, 3, 4, 5, 6, or another number of electrically isolated signal channels, each corresponding to a pin port 1345.

In some embodiments, each pin port 1345 may be associated with and arranged to electrically couple to a respective pin 1410 recessed within the socket 1400 of the stimulation generation device 1005, as depicted in FIG. 14, to thereby allow transcutaneous electrical stimulation to be delivered to the electrode connector assembly 1015, 1020. For example, the pins 1410 may be configured for insertion into the pin ports 1345.

As depicted in FIGS. 13A and 13B, in some embodiments, the projection portion 1325 of the connector plug 1315 may be substantially elongate and the pin ports 1345 may be aligned in a row along a major axis A-A of the projection portion 1325. Alternatively, the pin ports 1345 may be aligned in a column perpendicular to the major axis A-A of the projection portion 1325. In other embodiments, the pin ports 1345 may be arranged in any suitable configuration, for example, in a square or circular formation.

In some embodiments, the projection portion 1325 may include a notch 1350 configured to cooperate or align with a corresponding protrusion 1415 provided within a recess 1420 of the socket 1400 to assist a user to correctly orientate the connector plug 1315 for insertion into the socket 1400.

Studies involving some described embodiments are described by the following non-limiting prophetic example:

Example

This example involves the use of a system or kit of some described embodiments comprising a garment, a first and second electrode connector assembly and a stimulation device for delivering transcutaneous electrical stimulation to treat individuals with a faecal waste elimination dysfunction condition.

Patient Group:

The patient group includes individuals suffering from faecal waste elimination dysfunction of the gastrointestinal tract that have failed to respond significantly to medical treatments such as dietary modifications, oral and rectal laxatives. Given the diversity of human body shapes, individuals participating will be of a variety of body shapes and sizes associated with weight, age, ethnicity and gender.

Stimulation Regime:

Parents of the children, and/or adults with faecal waste elimination dysfunction of the gastrointestinal tract will be trained to use the system or kit for delivering transcutaneous electrical stimulation. Stimulation will be performed and monitored (for a variety of times, for example, including up to one hour for at least three times a week or greater for a minimum of 2 months). During the stimulation period the participants will be encouraged to continue to perform "normal activities" of daily life which may include a range of movements from standing to sitting or gentle play activities.

Outcome Measures:

The number of spontaneous and "sit" defecations, number of antegrade enema washouts, amount of medication (laxatives) and number of incidents of soiling will be recorded daily in a specially designed continence dairy. The daily dairy will be kept one month prior and for two months using flexible web in a plane, connector, and system during electrical stimulation. The (a) frequency of defecation, (b) frequency of soiling and (c) frequency of episodes of abdominal pain per month will be compared with post-test analysis and paired t-tests (two tailed).

In some embodiments, a successful treatment of a patient by administration of transcutaneous electrical stimulation treatment delivered using the system or kit of some of the described embodiments is one that may include at least one or more of the following features: (a) number of defecations have increased per week; (b) the number of soiling incidents decreased; (c) reduced use of laxatives; (d) changes in the consistency of the stool from hard to increased softness; and (e) increase in sensory awareness of urge to defecate.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of providing interferential transcutaneous electrical stimulation, the method comprising:
    positioning a first flexible web comprising a first plurality of electrodes at a lumbar area of a user;
    positioning a second flexible web comprising a second plurality of electrodes at a lower abdominal area of the user; and
    providing transcutaneous electrical stimulation to the first and second plurality of electrodes to create at least first and second electrical currents between the lumbar area and the lower abdominal area of the user,
    wherein the at least first and second electrical currents cross to create interferential transcutaneous electrical stimulation between the lower abdominal area and the lumbar area of the user.

2. The electrical stimulation method of claim 1, wherein providing transcutaneous electrical stimulation comprises providing the transcutaneous electrical stimulation to a first and second plurality of electrode connectors.

3. The electrical stimulation method of claim 2, wherein the first and second plurality of electrode connectors each comprises first, second, third and fourth electrode connectors.

4. The electrical stimulation method of claim 2, wherein each of the first and second flexible webs has a quadrilateral shape to define respective vertices, and wherein the first and second plurality of electrode connectors each comprise first, second, third and fourth electrode connectors positioned at the respective vertices.

5. The electrical stimulation method of claim 1, wherein positioning a first flexible web comprises putting a front portion of a wearable belt on the user, and positioning a second flexible web comprises putting a back portion of the wearable belt on the user.

6. The electrical stimulation method of claim 1, wherein the first and second flexible web each has a first face that is generally planar and an opposite second face.

7. The electrical stimulation method of claim 1, additionally comprising:
    supporting first and second conductors via respective first and second conductor support structures; and
    encasing at least part of each of the respective first and second conductors and at least partially encasing the respective first and second conductor support structures via a respective encasing material.

8. The electrical stimulation method of claim 7, additionally comprising coupling the first and second conductors to respective first and second electrical connectors.

9. The electrical stimulation method of claim 8, additionally comprising electrically coupling the first and second electrical connectors via a four-pole jack or a four pin port to a stimulation generation device.

10. The electrical stimulation method of claim 7, wherein at least one conductor of each of the first and second conductors passes through the respective conductor support structure.

11. A method of providing interferential transcutaneous electrical stimulation to a user, the method comprising:
  electrically coupling a first plurality of electrode connectors to respective mating connectors of a first electrode connector assembly of a wearable garment;
  electrically coupling a second plurality of electrode connectors to respective mating connectors of a second electrode connector assembly of the wearable garment;
  coupling together a first part of the wearable garment and a second part of the wearable garment such that the first plurality of electrode connectors are positioned at a lumbar area of the user and the second plurality of electrode connectors are positioned at a lower abdominal area of the user; and
  receiving electrical stimulation signals at the first and second electrode connectors to create first and second electrical currents between the first and second plurality of electrode connectors,
  wherein the first and second electrical currents cross to create interferential transcutaneous electrical stimulation between the lower abdominal area and the lumbar area.

12. The method of claim 11, further comprising receiving the first electrode connector assembly via an opening of a first pocket of the wearable garment.

13. The method of claim 11, further comprising receiving a stimulation generation device in a pocket of the wearable garment.

14. The method of claim 12, further comprising securing an electrical connector of the first electrode connector assembly with a first side pocket of the first pocket.

15. The method of claim 12, further comprising receiving the second electrode connector assembly via an opening of a second pocket of the wearable garment.

16. The method of claim 14, further comprising securing an electrical connector of the second electrode connector assembly with a second side pocket of the second pocket.

17. An electrical stimulation system for use in transcutaneous electrical stimulation, the system comprising:
  a first web configured to carry a first plurality of electrode connectors for positioning at a lumbar area of a user; and
  a second web configured to carry a second plurality of electrode connectors for positioning at an abdominal area of the user,
  wherein providing transcutaneous electrical stimulation to the first and second plurality of electrode connectors with the first web positioned at the lumbar area and the second web positioned at the lower abdominal area creates first and second electrical currents between the first and second plurality of electrode connectors that cross to create interferential transcutaneous electrical stimulation between the lower abdominal area and the lumbar area of the user.

18. The system of claim 17, wherein the first and second webs are flexible.

19. The system of claim 17, further comprising an electrical stimulation generation device configured to electrically couple with and provide the transcutaneous electrical stimulation to the first and second plurality of electrode connectors.

20. The system of claim 17, further comprising a wearable garment to carry the first and second webs.

* * * * *